United States Patent
Todoroki et al.

(10) Patent No.: US 10,125,095 B2
(45) Date of Patent: Nov. 13, 2018

(54) ABSCISIC ACID DERIVATIVE

(71) Applicant: NATIONAL UNIVERSITY CORPORATION SHIZUOKA UNIVERSITY, Shizuoka-shi, Shizuoka (JP)

(72) Inventors: Yasushi Todoroki, Shizuoka (JP); Naoki Mimura, Shizuoka (JP)

(73) Assignee: NATIONAL UNIVERSITY CORPORATION SHIZUOKA UNIVERSITY (JP)

( * ) Notice: Subject to any disclaimer, the term of this patent is extended or adjusted under 35 U.S.C. 154(b) by 0 days.

(21) Appl. No.: 15/513,765

(22) PCT Filed: Sep. 16, 2015

(86) PCT No.: PCT/JP2015/076335
§ 371 (c)(1),
(2) Date: Mar. 23, 2017

(87) PCT Pub. No.: WO2016/047532
PCT Pub. Date: Mar. 31, 2016

(65) Prior Publication Data
US 2017/0283375 A1    Oct. 5, 2017

(30) Foreign Application Priority Data
Sep. 24, 2014 (JP) ................... 2014-193597

(51) Int. Cl.
| | | |
|---|---|---|
| C07C 62/00 | (2006.01) | |
| C07C 403/22 | (2006.01) | |
| C07C 403/20 | (2006.01) | |
| A01N 37/36 | (2006.01) | |
| A01N 37/38 | (2006.01) | |

(52) U.S. Cl.
CPC ............ *C07C 403/22* (2013.01); *A01N 37/36* (2013.01); *A01N 37/38* (2013.01); *C07C 403/20* (2013.01)

(58) Field of Classification Search
None
See application file for complete search history.

(56) References Cited

U.S. PATENT DOCUMENTS

| | | | |
|---|---|---|---|
| 3,576,839 A | 4/1971 | Draber | 260/468 |
| 5,518,995 A | 5/1996 | Abrams et al. | 504/348 |
| 2010/0160166 A1 | 6/2010 | Abrams et al. | 504/289 |

FOREIGN PATENT DOCUMENTS

| | | |
|---|---|---|
| CN | 102391147 A | 3/2012 |
| EP | 0 371 882 A2 | 6/1990 |
| JP | H3-002102 A | 1/1991 |
| JP | H3-184966 A | 8/1991 |
| JP | 2014-511868 A | 5/2014 |
| WO | WO 94/15467 | 7/1994 |
| WO | WO 2012/139890 A1 | 10/2012 |

OTHER PUBLICATIONS

Notification of Transmittal of Translation of the International Preliminary Report on Patentability (Chapter I or Chapter II) for PCT/JP2015/076335 dated Mar. 30, 2017.
International Search Report for International Application No. PCT/JP2015/076335 dated Dec. 15, 2015.
Tadao Asami et al., "4'-Alkoxy derivatives of abscisic acid: a promising new probe for mechanisms of abscisic acid perceptions", Plant Growth Regulation, 2002, 38(3), p. 237-p. 241.
Jun Takeuchi et al., "Designed abscisic acid analo_gs as antagonists of PYL-PP2C receptor interactions", Nature Chemical Biology, 2014, vol. 10, p. 477-p. 482.
Office Action dated Dec. 4, 2017 issued in corresponding Chinese Patent Application No. 201580051292.4 (without English translation).

*Primary Examiner* — Ana Z Muresan
(74) *Attorney, Agent, or Firm* — Ostrolenk Faber LLP

(57) ABSTRACT

The compound represented by formula (IV) or a salt thereof has an inhibitory action on an abscisic acid receptor. The compound or the salt thereof can be used as a plant growth regulator.

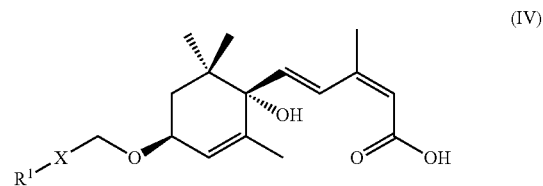

(IV)

wherein X is an ethylene group, an ethenylene group or an ethynylene group, $R^1$ is a hydrogen atom, a phenyl group or a naphthyl group, and the phenyl group and naphthyl group each optionally have a substituent selected from the group consisting of a halogen atom, a hydroxyl group, a C1-6 alkyl group, a C1-6 alkyl group substituted with a halogen atom, a C1-6 alkoxy group, an acetyl group, an amino group, an acetylamino group, a phenyl group and a pentafluorosulfanyl group.

12 Claims, 3 Drawing Sheets

(a) ABA not applied (b) ABA co-applied

ABSCISIC ACID DERIVATIVE

CROSS-REFERENCE TO RELATED APPLICATIONS

The present application is a 35 U.S.C. §§ 371 national phase conversion of PCT/JP2015/076335, filed Sep. 16, 2015, which claims priority to Japanese Patent Application No. 2014-193597, filed Sep. 24, 2014, the contents of both of which are incorporated herein by reference. The PCT International Application was published in the Japanese language.

TECHNICAL FIELD

The present invention relates to an abscisic acid derivative. More specifically, the present invention relates to an abscisic acid receptor antagonist.

BACKGROUND ART

Abscisic acid is a phytohormone playing an important role in the seed dormancy and the environmental stress response. The abscisic acid receptor, when bonded to abscisic acid, changes the three-dimensional conformation thereof and bonds to protein phosphatase PP2C to inhibit the enzyme activity thereof, thereby activating the signal transduction thereafter.

Abscisic acid receptor antagonists are expected to be applied to the agricultural field as the plant growth regulator and, in recent years, it has been reported that an abscisic acid derivative obtained by introducing an alkyl sulfanyl group into the 3'-position of abscisic acid has the abscisic acid receptor antagonistic action (Non Patent Literature 1).

CITATION LIST

Non Patent Literature

Non Patent Literature 1: Takeuchi et al., "Designed abscisic acid analogs as antagonists of PYL-PP 2C receptor interactions", Nature Chemical Biology, vol. 10, pp. 477-482 (2014)

SUMMARY OF INVENTION

Technical Problem

The present invention has an object to provide a novel abscisic acid receptor antagonist.

Solution to Problem

The present inventors have conducted extensive studies and found that an abscisic acid derivative in which the 4'-position oxo group of abscisic acid is replaced with a substituted or unsubstituted 2-propanyloxy group, 2-propenyloxy group or 2-propynyloxy group has the abscisic acid receptor antagonistic action, whereby the present invention has been accomplished.

More specifically, the present invention provides a compound represented by formula (IV) or a salt thereof:

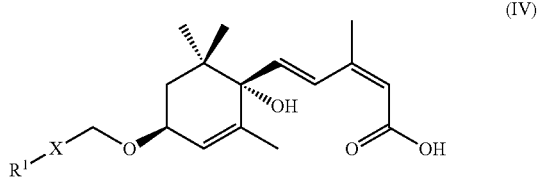

(IV)

wherein X is an ethylene group, an ethenylene group or an ethynylene group, $R^1$ is a hydrogen atom, a phenyl group or a naphthyl group, and the phenyl group and naphthyl group each optionally have a substituent selected from the group consisting of a halogen atom, a hydroxyl group, a C1-6 alkyl group, a C1-6 alkyl group substituted with a halogen atom, a C1-6 alkoxy group, an acetyl group, an amino group, an acetylamino group, a phenyl group and a pentafluorosulfanyl group.

Further, the present invention provides a compound represented by formula (I) or a salt thereof:

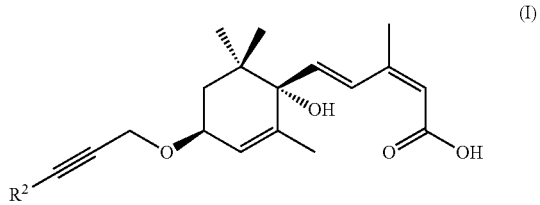

(I)

wherein $R^2$ is a hydrogen atom, a phenyl group or a naphthyl group, and the phenyl group and naphthyl group each optionally have a substituent selected from the group consisting of a halogen atom, a hydroxyl group, a C1-6 alkyl group, a C1-6 alkyl group substituted with a halogen atom, a C1-6 alkoxy group, an acetyl group, an amino group, an acetylamino group and a phenyl group.

In the above compound or the salt thereof, $R^2$ may be a phenyl group or a 1-naphthyl group.

The compound or the salt thereof can be used as an inhibitor of the abscisic acid receptor and also be used as a plant growth regulator.

Advantageous Effects of Invention

The compound represented by the formula (IV) or formula (I) or the salt thereof has an abscisic acid receptor antagonistic action and can be a plant growth regulator such as for controlling the seed germination.

DESCRIPTION OF EMBODIMENTS

Figure 1:
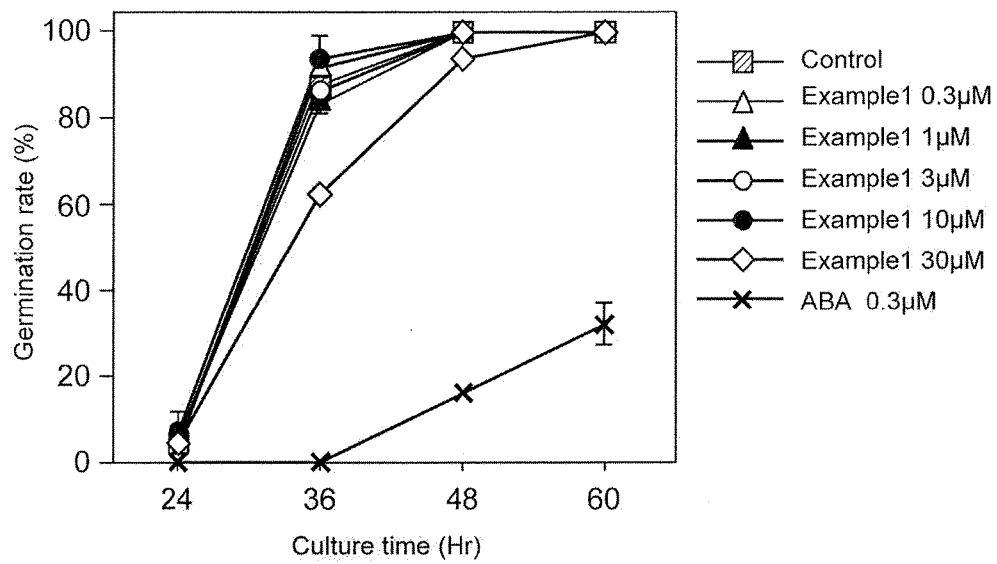
FIG. 1 includes graphs showing the examination results of the influence of the compound of Example 1 on the seed germination of thale cress.
Figure 1:
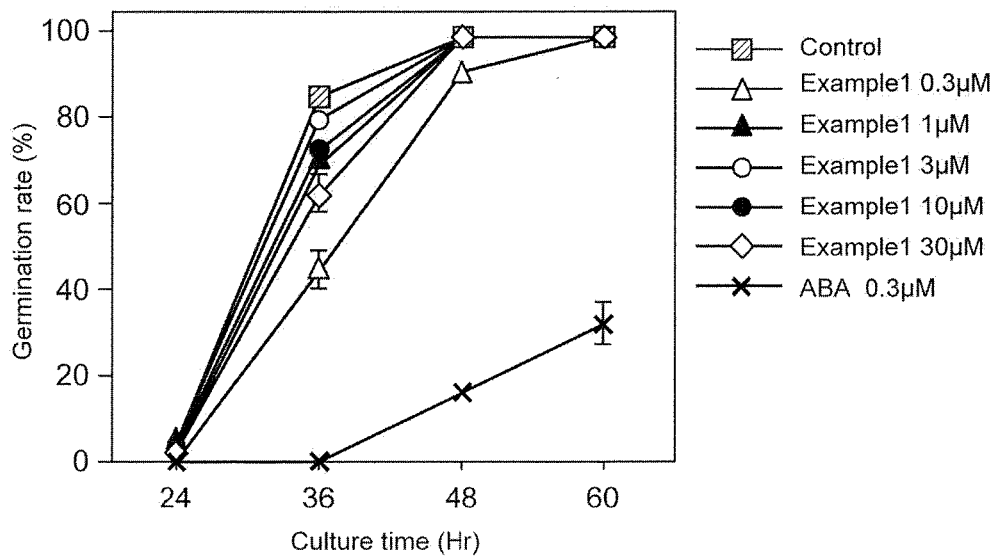

Hereinbelow, the terms herein used will be defined, and then the present invention will be described in details.

The "halogen atom" herein means a fluorine atom, a chlorine atom, a bromine atom and an iodine atom, with a fluorine atom and a chlorine atom being preferable.

The "C1-6 alkyl group" herein means a straight or branched alkyl group having 1 to 6 carbon atoms, and examples thereof include a methyl group, an ethyl group, an n-propyl group, an isopropyl group, an n-butyl group, an isobutyl group, a sec-butyl group, a tert-butyl group, an n-pentyl group, an isopentyl group, a neopentyl group and an n-hexyl group. The C1-6 alkyl group is, more preferably, a C1-3 alkyl group, which is a alkyl group having 1 to 3 carbon atoms, such as a methyl group, an ethyl group and an n-propyl group.

The "C1-6 alkyl groups substituted with a halogen atom" herein means a group formed by replacing one or more hydrogen atoms in a C1-6 alkyl group with halogen atoms, and examples thereof include fluoromethyl, difluoromethyl, trifluoromethyl, trichloromethyl, 1-fluoroethyl, 2-fluoroethyl, 2-chloroethyl, 1,2-difluoroethyl, 2,2-difluoroethyl, 2,2,2-trifluoroethyl, 1-fluoropropyl, 2-fluoropropyl, 3-fluoropropyl and 3-chloropropyl. The C1-6 alkyl group substituted with a halogen atom are, more preferably, a C1-3 alkyl group substituted with a halogen atom.

The "C1-6 alkoxy groups" herein means an oxy group to which a C1-6 alkyl group is bonded, and examples thereof include a methoxy group, an ethoxy group, a 1-propyloxy group, a 2-propyloxy group, a 1-butyloxy group, a 2-methylpropyloxy group, a 1-methylpropyloxy group, a 1,1-dimethylethoxy group.

The "naphthyl group" herein means a 1-naphthyl group or a 2-naphthyl group.

The compound according to the present embodiment is represented by the formula (IV). Hereinafter, the compound is sometimes referred to as the compound (IV).

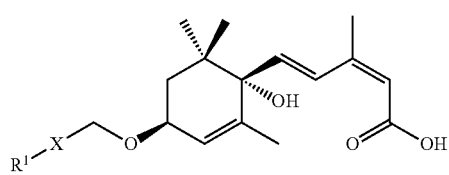

(IV)

wherein X is an ethylene group, an ethenylene group or an ethynylene group, $R^1$ is a hydrogen atom, a phenyl group or a naphthyl group, and the phenyl group and naphthyl group each optionally have a substituent selected from the group consisting of a halogen atom, a hydroxyl group, a C1-6 alkyl group, a C1-6 alkyl group substituted with a halogen atom, a C1-6 alkoxy group, an acetyl group, an amino group, an acetylamino group, a phenyl group and a pentafluorosulfanyl group.

The compound (IV) may be the compound represented by the formula (I) (hereinafter, also referred to as the "compound (I)"):

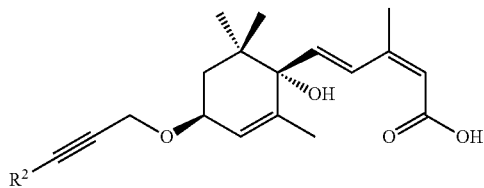

(I)

wherein $R^2$ is a hydrogen atom, a phenyl group or a naphthyl group, and the phenyl group and naphthyl group each optionally have a substituent selected from the group consisting of a halogen atom, a hydroxyl group, a C1-6 alkyl group, a C1-6 alkyl group substituted with a halogen atom, a C1-6 alkoxy group, an acetyl group, an amino group, an acetylamino group and a phenyl group.

When $R^1$ or $R^2$ is the phenyl group or the naphthyl group with a substituent, the substituent may be at any position and the number of the substituent may be one or more. When $R^1$ or $R^2$ is the phenyl group with a substituent, it is preferable that the number of the substituent is one and that the position of the substituent is the meta-position or the para-position.

$R^1$ is, preferably, a hydrogen atom, a phenyl group, a 1-naphthyl group, a 2-naphthyl group, a p-trifluoromethylphenyl group, a p-methoxyphenyl group, a p-acetyl phenyl group, a p-tolyl group, an m-tolyl group, a p-hydroxyphenyl group, a p-aminophenyl group, a p-acetylaminophenyl group, a p-chlorophenyl group, a p-biphenyl group or a p-pentafluorosulfanyl group.

$R^1$ is, more preferably, a hydrogen atom, a phenyl group, a 1-naphthyl group, a 2-naphthyl group, a p-trifluoromethylphenyl group, a p-methoxyphenyl group, a p-acetyl phenyl group, a p-tolyl group or a p-pentafluorosulfanyl group.

$R^1$ is, most preferably, a phenyl group, a p-tolyl group or a 1-naphthyl group.

$R^2$ is, preferably, a hydrogen atom, a phenyl group, a 1-naphthyl group, a 2-naphthyl group, a p-trifluoromethylphenyl group, a p-methoxyphenyl group, a p-acetyl phenyl group, a p-tolyl group, an m-tolyl group, a p-hydroxyphenyl group, a p-aminophenyl group, a p-acetylaminophenyl group, a p-chlorophenyl group or a p-biphenyl group.

$R^2$ is, more preferably, a hydrogen atom, a phenyl group, a 1-naphthyl group, a 2-naphthyl group, a p-trifluoromethylphenyl group, a p-methoxyphenyl group, a p-acetyl phenyl group or a p-tolyl group.

$R^2$ is, more preferably, a phenyl group, a p-tolyl group or a 1-naphthyl group.

X may be any of an ethylene group, an ethenylene group or an ethynylene group, with an ethylene group or an ethynylene group being preferable.

The compound (IV) may be in the form of a salt. Examples of the salt include inorganic base salts and organic base salts. Examples of the inorganic base salt include alkali metal salts such as sodium salts and potassium salts, alkaline earth metal salts such as calcium salts and magnesium salts, aluminium salts and ammonium salts. Examples of the organic base salt include diethylamine salts, diethanolamine salts, meglumine salts and N,N'-dibenzylethylenediamine salts.

The compound (I) can be produced by the following reaction scheme:

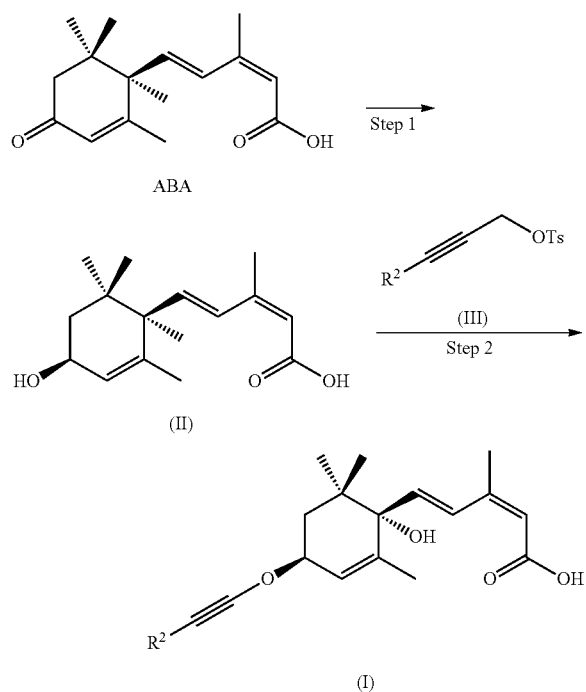

wherein Ts represents a tosyl group.

Step 1 is reducing an abscisic acid (hereinafter, sometimes referred to as ABA) to obtain a compound (II) by. The reaction of Step 1 can be carried out using a reducing agent capable of achieving the reduction from ketone to alcohol under the reaction conditions (reaction solvent, reaction temperature and reaction time) commonly employed for the reduction reaction. Examples of the reducing agent include sodium borohydride and lithium aluminium hydride. Examples of the specific reaction condition include those described in Production Example 1.

Step 2 is reacting the compound (II) with a compound (III) to obtain the compound (I). The reaction is carried out in the presence of a base such as sodium hydride. For example, making reference to Example 1 for the reaction conditions, the reaction of Step 2 can be carried out. The compound (I) obtained in the form of a free base can be converted to a salt by a routine method. Similarly, the compound (1) obtained in the form of a salt can be converted to a free base by a routine method.

The compound (III) can be produced easily by those skilled in the art using commercial compounds as raw materials. For example, making reference to Production Example 2 for the reaction conditions, the compound (III) can be produced.

The compound (IV) can be produced by the same method as the compound (I). For example, the compound (IV) can be obtained by reacting the compound (II) with a compound represented by formula (V) (hereinafter, also referred to as "compound (V)"). Examples of the specific reaction condition include those described in Example 9. The compound (IV) obtained in the form of a free base can be converted to a salt by a routine method. Similarly, the compound (IV) obtained in the form of a salt can be converted to a free base by a routine method.

$$R^1 \diagdown X \diagdown OTs \quad (V)$$

wherein X is an ethylene group, an ethenylene group or an ethynylene group, $R^1$ is a hydrogen atom, a phenyl group or a naphthyl group, and the phenyl group and naphthyl group each optionally have a substituent selected from the group consisting of a halogen atom, a hydroxyl group, a C1-6 alkyl group, a C1-6 alkyl group substituted with a halogen atom, a C1-6 alkoxy group, an acetyl group, an amino group, an acetylamino group, a phenyl group and a pentafluorosulfanyl group.

The compound (V) can be produced easily by those skilled in the art using commercial compounds as raw materials. For example, making reference to Production Example 3 for the reaction conditions, the compound (V) can be produced.

The compound (IV) has the abscisic acid receptor antagonistic action and hence can also be used as an inhibitor of the abscisic acid receptor. The abscisic acid receptor means any receptors belonging to the protein family known as PYR/PYL/RCAR proteins.

Typically, in a plant, PP2C dephosphorylates protein kinase SnRK2 to maintain an inactive state. When a plant is exposed to stresses, the abscisic acid is synthesized and delivered to a target organ, followed by bonding to an abscisic acid receptor. When the abscisic acid bonds to the abscisic acid receptor, the abscisic acid receptor forms a conjugate with PP2C thereby suppressing the dephosphorylation by PP2C. Consequently, SnRK2 autophosphorylates to changes to an activated state and thus activates the downstream ion channel and the transcription factors, thereby inducing the abscisic acid response.

In the compound (IV)-applied plant, the compound (IV) inhibits the bonding between the abscisic acid and the abscisic acid receptor and the subsequent conjugate formation with PP2C, so that the abscisic acid response is not induced even when the abscisic acid is synthesized due to stresses. Thus, the compound (IV) can regulate the plant growth.

As described above, the compound (IV) can be a plant growth regulator. The plant growth is not particularly limited as long as it is the phenomenon involving the typical differentiation or growth of a plant cell and encompasses not only extension and expansion of the organs structuring a plant body but also seed germination, flower bud formation and seed development.

The target plant is not particularly limited and may be seed plants, pteridophytes or bryophytes. The seed plants may be gymnosperms or angiosperms, and the angiosperms may be monocotyledons or dicotyledons.

The target plant organ is not particularly limited and may be any of roots, stems, leaves, flowers, reproductive organs, seeds, and may further be cultured cells.

The concentration and contact method of the compound (IV) applied to a plant can be suitably adjusted depending on the kind and organ of a target plant and the purpose. For example, when the target plant and the target organ are a dicotyledon and a seed, respectively, for the purpose of seed germination, it is preferable to cultivate using a culture broth obtained by dissolving the compound (IV) in the typical culture broth to a concentration of 0.3 to 300 µM.

The plant growth regulator containing the compound (IV) may contain, in addition to the compound (IV), a germicide, an antifungal agent, an insecticide or a compound having the plant growth regulation action other than the compound (IV). The regulator may further contain known preparation additives. Examples of the preparation additives include an excipient, an emulsifier and a wetting agent. The form of the plant growth regulator of the present invention is not particularly limited and may be, for examples, an emulsion, a wettable powder, a water soluble powder, a liquid, a granule, a dust, a microcapsule, a fumigant, a smoking agent, an aerosol, a flowable, a paste, a tablet, a coating agent, an agent for ultra-low volume spraying, an oil agent or a compounded fertilizer, from which a user can suitably select in accordance with a target plant and organ thereof and a purpose. The plant growth regulator in these forms can be produced by a known method.

EXAMPLE

[Production Example 1] Synthesis of (2Z,4E)-5-((1S,4S)-1,4-dihydroxy-2,6,6-trimethylcyclohex-2-en-1-yl)-3-methylpenta-2,4-dienoic acid

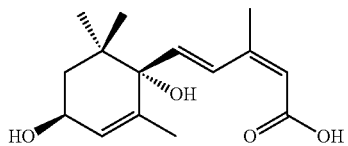

11.2 g of S-abscisic acid (purity 90%) (10 g, 37.8 mmol in terms of S-abscisic acid) was dissolved in 400 mL of methanol. 42.9 g (115.1 mmol) of cerium (III) chloride heptahydrate was added thereto and dissolved and subsequently 14.7 g (389 mmol) of sodium borohydride was slowly added while cooling in an ice bath. The solution was heated to room temperature and stirred for 15 minutes, and subsequently 200 mL of a saturated aqueous solution of ammonium chloride was added while cooling in an ice bath thereby terminating the reaction, followed by concentrating the reaction solution under reduced pressure using an evaporator to remove methanol. 200 mL of 2M hydrochloric acid was added thereto, followed by confirming the pH of the reaction solution to be 1 to 2 using a pH test paper, and 400 mL of distilled water was added thereto to partition-extract three times with 600 mL of ethyl acetate. The resultant was washed three times with a saturated aqueous solution of sodium chloride, dried over sodium sulfate, and concentrated thereby obtaining 16.87 g of a white solid. The solid was subjected to silica gel column chromatography (365 g, 4 cm inner diameter×30 cm length) using hexane-ethyl acetate (0-30-50%, step gradient) as an eluent thereby obtaining an intended product (white solid, 4.35 g) and a mixture of the intended product and impurities (white solid, 6.58 g) and subsequently only the mixture with impurities was further subjected to silica gel column chromatography (995 g, 3 cm inner diameter×33 cm length) using hexane-ethyl acetate (0-30-65%, step gradient) as an eluent thereby obtaining 1.38 g (total 5.73 g, yield 56%) of the titled compound.

$^1$H NMR (270 MHz, CD$_3$OD): δ 0.81 (3H, s), 0.92 (3H, s), 1.51 (1H, dd, J=13.2 and 9.9 Hz), 1.55 (3H, d, J=1.65 Hz), 1.63 (1H, ddd, J=13.2, 6.6 and 1.3 Hz), 1.92 (3H, d, J=1.3 Hz), 4.09 (1H, m), 5.43 (1H, m), 5.60 (1H, q, J=1.0 Hz), 6.12 (1H, dd, J=16.2 and 0.7 Hz), 7.58 (1H, dd, J=16.2 and 0.7 Hz)

[Production Example 2] Synthesis of 4-methylbenzene sulfonic acid 3-phenylprop-2-yn-1-yl

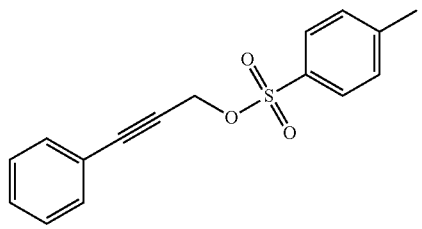 [SMILES: Cc1ccc(S(=O)(=O)OCC#Cc2ccccc2)cc1]

8.0 g (39.2 mmol) of iodobenzene was dissolved in 50 mL of tetrahydrofuran, and 7.93 g (78.4 mmol) of triethylamine, 566 mg (0.784 mmol) of bis(triphenylphosphine)palladium (II) dichloride and 519 mg (2.74 mmol) of copper(I) iodide were added thereto while cooling in an ice bath, followed by stirring for 30 minutes. To the resultant solution, 10 mL of a solution of 2.20 g (39.2 mmol) of propargyl alcohol in tetrahydrofuran was added using a dropping funnel, followed by heating to room temperature, and the resultant solution was stirred for 30 minutes and passed through a short column (silica gel 64-210 μm diameter, 1.5 cm inner diameter×25 cm height) thereby terminating the reaction. The obtained solution was washed three times with a saturated aqueous solution of sodium chloride, dried over sodium sulfate, and concentrated thereby obtaining 6.29 g of a brownish oily substance. The oily substance was subjected to silica gel column chromatography (289 g, 2.1 cm inner diameter×40 cm length) using hexane-ethyl acetate (0-20-100%, step gradient) as an eluent thereby obtaining 3-phenylprop-2-yn-1-ol (a brownish oily substance, 4.56 g) (yield 88%). 4.00 g (30.3 mmol) of 3-phenylprop-2-yn-1-ol was dissolved in 8 mL of tetrahydrofuran. To the resultant solution, 20 mL of a solution of 12.3 g (121 mmol) of triethylamine and 11.8 g (60.6 mmol) of p-toluenesulfonyl chloride in tetrahydrofuran was added under a condition of −10° C. The solution was heated to 0° C. and stirred for 90 minutes, and subsequently the reaction solution was added to a separatory funnel containing 400 mL of ethyl acetate. 20 mL of 1M hydrochloric acid was added thereto, and the separatory funnel was shaken thoroughly to remove triethylamine. The same operation was repeated again and the solution was washed four times with a saturated aqueous solution of sodium chloride, dried over sodium sulfate, and concentrated thereby obtaining 10.0 g of a brownish oily substance. The oily substance was subjected to silica gel column chromatography (995 g, 4.1 cm inner diameter×38 cm length) using hexane-ethyl acetate (0-10%, step gradient) as an eluent thereby obtaining 3.60 g (yield 42%) of the titled compound.

$^1$H NMR (270 MHz, CDCl$_3$): δ 2.39 (3H, s), 4.95 (2H, s), 7.24-7.37 (7H, m), 7.85 (2H, m)

[Production Example 3] Synthesis of 4-methylbenzene sulfonic acid 3-phenylpropan-1-yl

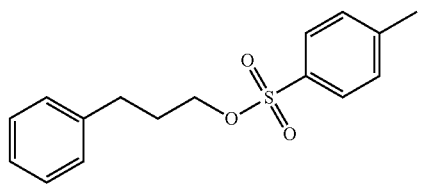 [SMILES: Cc1ccc(S(=O)(=O)OCCCc2ccccc2)cc1]

200 mg (1.47 mmol) of 3-phenyl-1-propanol was dissolved in 2 mL of dichloromethane, and 339.6 mg (1.78 mmol) of paratoluenesulfonyl chloride and 178.1 mg (1.76 mmol) of triethylamine were added thereto. The solution was stirred at room temperature for 2 hours, followed by adding 8 mL of distilled water and 2 mL of 1M hydrochloric acid thereto, and the resultant solution was partition-extracted three times with 10 mL of ethyl acetate. The resultant was washed three times with a saturated aqueous solution of sodium chloride, dried over sodium sulfate, and filtered using cotton, and the filtrate was concentrated under reduced pressure thereby obtaining 475 mg of a colorless clear oily substance. The oily substance was subjected to silica gel column chromatography (Wakosil C-200 9.21 g, 16 mm inner diameter×95 mm length) using hexane-ethyl acetate (1:9) as an eluent thereby obtaining 339.3 mg (yield 79%) of the titled compound.

$^1$H NMR (270 MHz, CDCl$_3$): δ 1.91 (2H, m), 2.45 (3H, s), 2.60 (2H, t, J=7.6 Hz), 4.00 (2H, t, J=6.3 Hz), 7.04-7.23 (5H, m), 7.43 (2H, m), 7.78 (2H, m)

[Example 1] Synthesis of (2Z,4E)-5-((1S,4S)-1-hydroxy-2,6,6-trimethyl-4-((3-phenylprop-2-yn-1-yl)oxy)cyclohex-2-en-1-yl)-3-methylpenta-2,4-dienoic acid

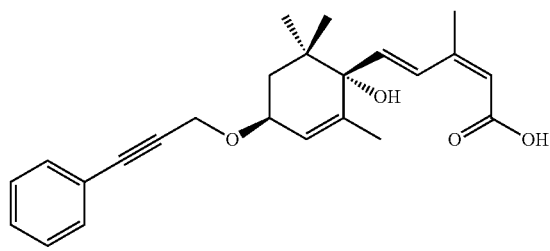

2.78 g (1.67 g, 64.8 mmol in terms of sodium hydride) of sodium hydride (oily dispersion 60%) was dissolved in 100 mL of hexane, followed by removing the supernatant. To the resultant solution, 50 mL of tetrahydrofuran was added and, after removing the supernatant, 200 mL of tetrahydrofuran was added to the resultant. 5.72 g (21.5 mmol) of (2Z,4E)-5-((1S,4S)-(1,4-dihydroxy-2,6,6-trimethylcyclohex-2-en-1-yl)-3-methylpenta-2,4-dienoic acid was added thereto while cooling in an ice bath, followed by stirring the solution for 30 minutes, and further 40 mL of a solution of 3.09 g (10.8 mmol) of 4-methylbenzene sulfonic acid 3-phenylprop-2-yn-1-yl in tetrahydrofuran was added thereto. The solution was heated to room temperature and stirred for 44 hours, and 100 mL of 2M hydrochloric acid was added thereto while cooling in an ice bath thereby terminating the reaction. The reaction solution was added to 900 mL of distilled water and partition-extracted three times with 600 mL of ethyl acetate. The resultant was washed three times with a saturated aqueous solution of sodium chloride, dried over sodium sulfate and concentrated thereby obtaining 8.34 g of a brownish oily substance. The oily substance was subjected to silica gel column chromatography (1039 g, 4.1 cm inner diameter×39 cm length) using hexane-ethyl acetate (0-20-40%, step gradient) as an eluent thereby obtaining a mixture of impurities and the intended product (a brownish oily substance, 2.34 g), and the mixture was further subjected to silica gel column chromatography (398 g, 2.5 cm inner diameter×40 cm length) using dichloromethane-ethyl acetate (30%) as an eluent thereby obtaining 1.375 g (yield 33%) of the titled compound.

$^1$H NMR (500 MHz, CDCl$_3$): δ 0.92 (3H, s, H3-9'), 1.06 (3H, s, H3-8'), 1.67 (3H, m, H3-7'), 1.72 (1H, dd, J=13.1 and 9.5 Hz, H-5'), 1.90 (1H, m, H-5'), 2.01 (3H, d, J=0.6 Hz, H3-6), 4.27 (1H, m, H-4'), 4.42 (1H, d, J=15.9 Hz, H-1"), 4.47 (1H, d, J=15.9 Hz, H-1"), 5.68 (1H, brs, H-3'), 5.71 (1H, s, H-2), 6.21 (1H, d, J=15.9 Hz, H-5), 7.31 (3H, m, H-6", 7" and 8"), 7.44 (2H, m, H-5" and 9"), 7.74 (1H, d, J=15.9 Hz, H-4)

$^{13}$C NMR (125 MHz, CDCl$_3$): δ 17.7 (C7'), 21.5 (C6), 22.7 (C8'), 25.3 (C9'), 39.7 (C6'), 40.7 (C5'), 56.1 (C1"), 72.3 (C4'), 79.3 (C1'), 85.5 (C2"), 86.0 (C3"), 117.0 (C2), 122.7 (C4"), 124.6 (C3'), 126.5 (C4), 128.3 (C6" and 8"), 128.4 (C7"), 131.7 (C5" and 9"), 139.1 (C2'), 140.3 (C5), 152.2 (C3), 170.6 (C1)

UV λ max (MeOH) nm(ε): 242.4 (27600), 250.4 (29000)

HRMS (m/z): [M+Na]$^+$ calc'd. for C24H28O4Na, 403.1885; found, 403.1880.

[Example 2] Synthesis of (2Z,4E)-5-((1S,4S)-1-hydroxy-2,6,6-trimethyl-4-((3-naphthalene-1-yl)prop-2-yn-1-yl)oxy)cyclohex-2-en-1-yl)-3-methylpenta-2,4-dienoic acid

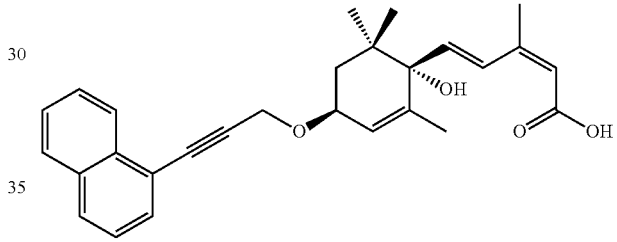

The reaction was carried out in the same manner as in Production Example 1 using S-abscisic acid-methyl in place of S-abscisic acid thereby obtaining 865.9 mg (yield 75.5%) of methyl (2Z,4E)-5-((1S,4S)-1,4-dihydroxy-2,6,6-trimethylcyclohex-2-en-1-yl)-3-methylpenta-2,4-dienoic acid. 30.0 mg (0.107 mmol) of methyl (2Z,4E)-5-((1S,4S)-1,4-dihydroxy-2,6,6-trimethylcyclohex-2-en-1-yl)-3-methylpenta-2,4-dienoic acid was dissolved in 1.0 mL of tetrahydrofuran, and 8.6 mg (5.22 mg, 0.214 mmol in terms of sodium hydride) of sodium hydride (oily dispersion 60%) was added thereto while cooling in an ice bath, followed by stirring the resultant solution for 30 minutes. To the solution, 26.2 mg (0.107 mmol) of 1-(3-bromoprop-1-yn-1-yl)naphthalene was added, and the resultant solution was heated to room temperature. After stirring for 4 hours, the reaction solution was added to 30 mL of a saturated aqueous solution of ammonium chloride thereby terminating the reaction, and the resultant solution was partition-extracted three times with ethyl acetate. The resultant was washed three times with a saturated aqueous solution of sodium chloride and dried over sodium sulfate thereby obtaining 55.4 mg of a light yellow oily substance. The oily substance was subjected to silica gel column chromatography (5 g, 0.5 cm inner diameter×28 cm length) using hexane-ethyl acetate (0-20-30-100%, step gradient) as an eluent thereby obtaining methyl (2Z,4E)-5-((1S,4S)-1-hydroxy-2,6,6-trimethyl-4-((3-naphthalene-1-yl)prop-2-yn-1-yl)oxy)cyclohex-2-en-1-yl)-3-methylpenta-2,4-dienoic acid (a light yellow oily substance, 3 mg) (yield 3%). The obtained substance was dissolved in 1.5 mL of methanol, and 1.8 mL of 1M sodium hydride was added thereto while cooling in an ice bath, followed by stirring the resultant solution for 3.5 hours. To the solution, 2 mL of 1M hydrochloric acid was added to terminate the reaction, and 30 mL of distilled water was added thereto. The resultant solution was partition-extracted three times with 20 mL of ethyl acetate, and the resultant was washed three times with saturated sodium chloride, dried over sodium sulfate, and concentrated thereby obtaining 5.6 mg of a light yellow oily substance. The oily substance was subjected to silica gel column chromatography (2 g, 0.5 cm inner diameter×15 cm length) using hexane-ethyl acetate (0-30-40%, step gradient) as an eluent thereby obtaining 0.8 mg (yield 27.5%) of the titled compound.

$^1$H NMR (500 MHz, CD$_3$OD): δ 0.95 (3H, s, H3-9'), 1.07 (3H, s, H3-8'), 1.70 (3H, dd, J=1.5 and 1.5 Hz, H3-7'), 1.76 (1H, dd, J=13.1 and 9.8 Hz, H-5'), 1.92 (1H, ddd, J=13.1, 6.4 and 1.5 Hz, H-5'), 2.01 (3H, d, J=1.2 Hz, H3-6), 4.41 (1H, m, H-4'), 4.60 (2H, d, J=1.5 Hz, OCH2-), 5.70 (1H, brs, H-2), 5.73 (1H, m, H-3'), 6.22 (1H, d, J=16.2 Hz, H-5), 7.44 (1H, dd, J=8.2 and 7.3 Hz, H-6"), 7.54 (2H, m, H-10" and 11"), 7.65 (1H, dd, J=7.3 and 1.2 Hz, H-5"), 7.73 (1H, d, J=16.2 Hz, H-4), 7.88 (2H, m, H-7" and 12"), 8.30 (1H, d, J=8.2 Hz, H-9")

$^{13}$C NMR (125 MHz, CD$_3$OD): δ 18.4 (C7'), 21.4 (C6), 23.3 (C8'), 25.7 (C9'), 40.9 (C6'), 41.7 (C5'), 56.8 (C1"), 74.1 (C4'), 80.2 (C1'), 84.8 (C2"), 91.9 (C3"), 118.8 (C2), 121.5 (C8"), 125.6 (C3'), 126.3 (C6"), 126.9 (C9"), 127.5 (C11"), 127.9 (C10"), 128.2 (C4), 129.4 (C12"), 130.0 (C7"), 131.5 (C5"), 134.6 (C4" or 13"), 134.7 (C4" or 13"), 141.1 (C5), 141.2 (C2'), 151.4 (C3), 169.8 (C1)

UV λ max (MeOH) nm (ε): 226.8 (59700), 262.2 (18000), 297.0 (13700), 310.4 (8410)

HRMS (m/z): [M+Na]$^+$ calc'd. for C28H30O4Na, 453.2042; found 453.2045.

[Example 3] Synthesis of (2Z,4E)-5-((1S,4S)-1-hydroxy-2,6,6-trimethyl-4-(prop-2-yn-1-yloxy)cyclohex-2-en-1-yl)-3-methylpenta-2,4-dienoic acid

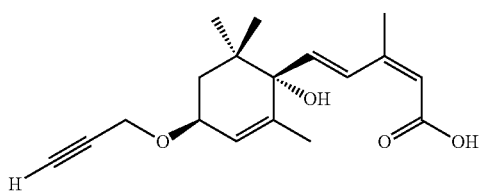

The reaction was carried out in the same manner as in Example 1 using 4-methylbenzene sulfonic acid prop-2-yn-1-yl in place of 4-methylbenzene sulfonic acid 3-phenylprop-2-yn-1-yl thereby obtaining the titled compound (yield 9%).

$^1$H NMR (270 MHz, CDCl$_3$): δ 0.92 (3H, s, H3-8' or 9'), 1.05 (3H, s, H3-8' or 9'), 1.63-1.71 (4H, m, H3-7' and H-5), 1.86 (1H, ddd, J=13.2, 6.6 and 1.3 Hz, H-5'), 2.02 (3H, d, J=1.0 Hz, H3-6), 2.43 (1H, t, J=2.3 Hz, H-3"), 4.16-4.23 (3H, m, H-4' and H2-1"), 5.64 (1H, m, H-3'), 5.72 (1H, s, H-2), 6.19 (1H, d, J=16.2 Hz, H-5), 7.35 (1H, d, J=16.2 Hz, H-4)

[Example 4] Synthesis of (2Z,4E)-5-((1S,4S)-1-hydroxy-2,6,6-trimethyl-4-((3-(4-trifluoromethyl)phenylprop-2-yn-1-yl)oxy)cyclohex-2-en-1-yl)-3-methylpenta-2,4-dienoic acid

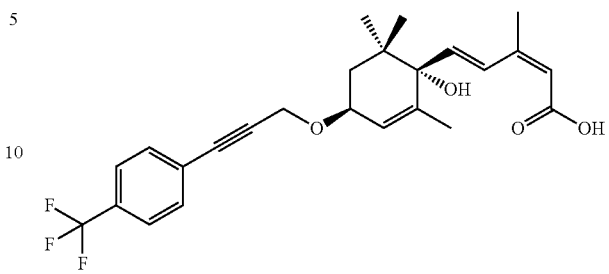

The reaction was carried out in the same manner as in Example 1 using 4-methylbenzene sulfonic acid 3-(4-trifluoromethyl)phenylprop-2-yn-1-yl) in place of 4-methylbenzene sulfonic acid 3-phenylprop-2-yn-1-yl thereby obtaining the titled compound (yield 18%).

$^1$H NMR (270 MHz, CDCl$_3$): δ 0.93 (3H, s), 1.07 (3H, s), 1.63-1.73 (4H, m), 1.82-1.93 (1H, m), 2.02 (3H, s), 4.14-4.29 (3H, m), 5.68 (1H, m), 5.71 (1H, s), 6.20 (1H, d, J=16.1 Hz), 7.52-7.60 (4H, m), 7.74 (1H, d, J=16.1 Hz),

[Example 5] Synthesis of (2Z,4E)-5-((1S,4S)-1-hydroxy-2,6,6-trimethyl-4-((3-(4-methoxy)phenylprop-2-yn-1-yl)oxy)cyclohex-2-en-1-yl)-3-methylpenta-2,4-dienoic acid

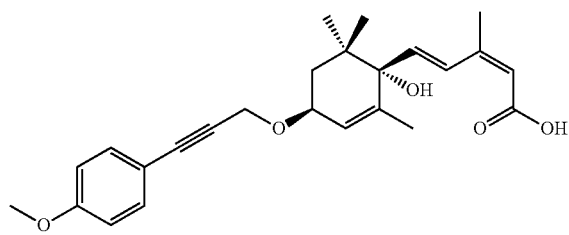

The reaction was carried out in the same manner as in Example 1 using 4-methylbenzene sulfonic acid 3-(4-methoxy)phenylprop-2-yn-1-yl in place of 4-methylbenzene sulfonic acid 3-phenylprop-2-yn-1-yl thereby obtaining the titled compound (yield 3%).

$^1$H NMR (270 MHz, CDCl$_3$): δ 0.90 (3H, s), 1.04 (3H, s), 1.65 (3H, s), 1.70 (1H, dd, J=12.5 and 9.6 Hz), 1.89 (1H, dd, J=12.5 and 6.6 Hz), 1.99 (3H, s), 3.85 (3H, s), 4.24 (1H, m), 4.36-4.48 (2H, m), 5.66 (1H, s), 5.71 (1H, s), 6.16 (1H, s), 6.81-6.87 (2H, m), 7.35-7.41 (2H, m), 7.73 (1H, s)

[Example 6] Synthesis of (2Z,4E)-5-((1S,4S)-1-hydroxy-2,6,6-trimethyl-4-((3-(4-acetyl)phenylprop-2-yn-1-yl)oxy)cyclohex-2-en-1-yl)-3-methylpenta-2,4-dienoic acid

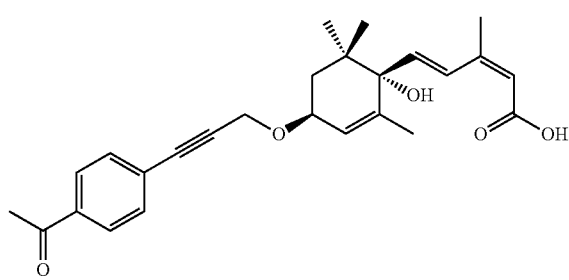

The reaction was carried out in the same manner as Example 1 using 4-methylbenzene sulfonic acid 3-(4-acetyl)phenylprop-2-yn-1-yl in place of 4-methylbenzene sulfonic acid 3-phenylprop-2-yn-1-yl thereby obtaining the titled compound (yield 0.5%).

$^1$H NMR (270 MHz, CDCl$_3$): δ 0.93 (3H, s), 1.07 (3H, s), 1.68 (3H, s), 1.72 (1H, dd, J=13.5 and 9.6 Hz), 1.90 (1H, dd, J=13.5 and 6.9 Hz), 2.02 (3H, s), 2.60 (3H, s), 4.25 (1H, m), 4.46 (2H, m), 5.69 (1H, s), 5.72 (1H, s), 6.21 (1H, d, J=16.2 Hz), 7.50-7.53 (2H, m), 7.74 (1H, d, J=16.2 Hz), 7.89-7.92 (2H, m)

[Example 7] Synthesis of (2Z,4E)-5-(1S,4S)-1-hydroxy-2,6,6-trimethyl-4-((3-(4-methyl)phenylprop-2-yn-1-yl)oxy)cyclohex-2-en-1-yl)-3-methylpenta-2,4-dienoic acid

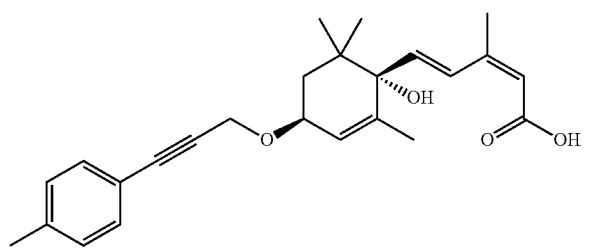 [SMILES: CC1=C[C@@H](OCC#Cc2ccc(C)cc2)CC(C)(C)[C@@]1(O)/C=C/C(C)=C\C(=O)O]

The reaction was carried out in the same manner as in Example 1 using 4-methylbenzene sulfonic acid 3-(4-methyl)phenylprop-2-yn-1-yl in place of 4-methylbenzene sulfonic acid 3-phenylprop-2-yn-1-yl thereby obtaining the titled compound (yield 18%).

$^1$H NMR (500 MHz, CDCl$_3$): δ 0.91 (3H, s), 1.05 (3H, s), 1.66 (3H, m), 1.71 (1H, dd, J=13.1 and 9.8 Hz), 1.89 (1H, m), 2.00 (3H, s), 2.34 (3H s), 4.26 (1H, m), 4.41 (1H, d, J=15.9 Hz), 4.45 (1H, d, J=15.9 Hz), 5.67 (1H, s), 5.71 (1H, s), 6.19 (1H, d, J=15.9 Hz), 7.10-7.12 (3H, m), 7.32-7.34 (2H, m), 7.74 (1H, d, J=15.9 Hz)

[Example 8] Synthesis of (2Z,4E)-5-(1S,4S)-1-hydroxy-2,6,6-trimethyl-4-((3-(4-trifluorosulfanyl)phenylprop-2-yn-1-yl)oxy)cyclohex-2-en-1-yl)-3-methylpenta-2,4-dienoic acid

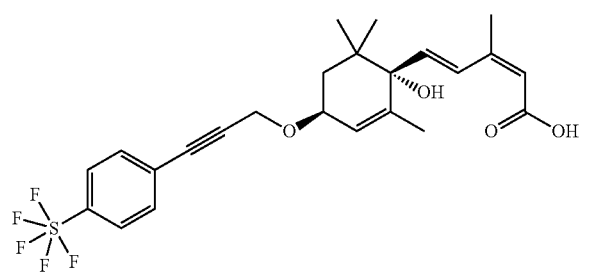 [SMILES: CC1=C[C@@H](OCC#Cc2ccc(S(F)(F)(F)(F)F)cc2)CC(C)(C)[C@@]1(O)/C=C/C(C)=C\C(=O)O]

3.2 mg (17 nmol) of copper(I) iodide, 3.2 mg (4.6 nmol) of trans-dichlorobis(triphenylphosphine)palladium (II), 1.0 mL of triethylamine and 1 mL of a solution of 75.6 mg (229 nmol) of 4-iodophenylsulphur pentafluoride in tetrahydrofuran were added to 2 mL of a solution of 72.0 mg (237 nmol) of (2Z,4E)-5-((1S,4S)-1-hydroxy-2,6,6-trimethyl-4-(prop-2-yn-1-yl)oxy)cyclohex-2-en-1-yl)-3-methylpenta-2,4-dienoic acid in tetrahydrofuran. The solution was stirred at room temperature for 6 hours, subsequently 5 mL of an aqueous solution of 1M hydrochloric acid was added thereto and the reaction solution was partition-extracted three times with 20 mL of ethyl acetate. The resultant was washed three times with a saturated aqueous solution of sodium chloride, dried over sodium sulfate, and concentrated thereby obtaining 114 mg of a brownish oily substance. The oily substance was subjected to silica gel column chromatography (12 g, 14 mm inner diameter×160 mm length) using dichloromethane-ethyl acetate (0-20%, step gradient) as an eluent thereby obtaining 53 mg of a mixture of the intended product and impurities. The mixture was further subjected to high performance liquid chromatography (Hydrosphere C 18, 20 mm inner diameter×150 mm length) using 77% methanol as an eluate thereby obtaining 30.3 mg (yield 25%) of the titled compound.

$^1$H NMR (500 MHz, CD$_3$OD): δ 0.94 (3H, s), 1.04 (3H, s), 1.68 (3H, m), 1.69 (1H, dd, J=13.0 and 9.3 Hz), 1.84 (1H, ddd, J=13.0, 6.4 and 1.5 Hz), 2.01 (3H, d, J=0.9 Hz), 4.27 (1H, m), 4.45 (1H, d, J=16.4 Hz), 4.49 (1H, d, J=16.4 Hz), 5.66 (1H, m), 5.71 (1H, m), 6.17 (1H, d, J=16.1 Hz), 7.58-7.60 (2H, m), 7.68 (1H, d, J=16.1 Hz), 7.79-7.82 (2H, m)

[Example 9] Synthesis of (2Z,4E)-5-(1S,4S)-1-hydroxy-2,6,6-trimethyl-4-((3-phenylpropan-1-yl)oxy)cyclohex-2-en-1-yl)-3-methylpenta-2,4-dienoic acid

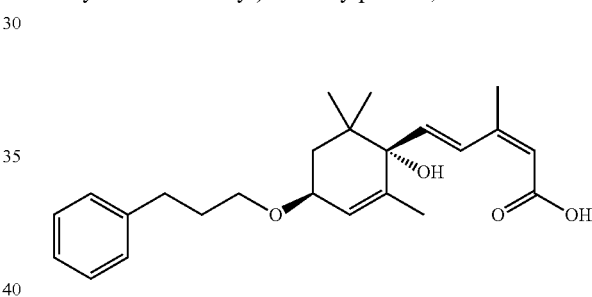

The reaction was carried out in the same manner as in Example 1 using 4-methylbenzene sulfonic acid 3-phenylpropan-1-yl in place of 4-methylbenzene sulfonic acid 3-phenylprop-2-yn-1-yl thereby obtaining the titled compound (yield 44%).

$^1$H NMR (500 MHz, CDCl$_3$): δ 0.91 (3H, s), 1.00 (3H, s), 1.62 (1H, dd), 1.66 (3H, s), 1.75 (1H, ddd, J=13.2, 6.3 and 1.0 Hz), 1.85 (2H, m), 2.01 (3H, s), 2.68 (2H, t, J=7.3 Hz), 3.49 (2H, m), 3.96 (1H, m), 5.58 (1H, m), 5.73 (1H, brs), 6.17 (1H, d, J=15.2 Hz), 7.20 (5H, m), 7.68 (1H, d, J=15.2 Hz)

[Comparative Example 1] Synthesis of 3'-hexylsulfanyl-abscisic acid

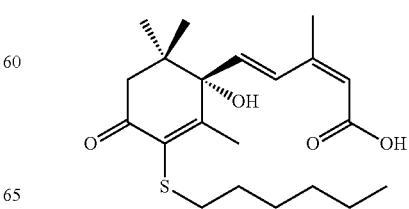

The titled compound was synthesized in accordance with the method described in Non Patent Literature 1.

[Test Example 1] Thale Cress Seed Germination Test (1)

Seeds of thale cress (*Arabidopsis thaliana*, Col-0) were immersed in 500 µL of an aqueous solution of 70% ethanol for 30 minutes, subsequently in 500 µL of a 100% ethanol solution for 1 minute, washed five times in 1 mL of distilled water, then immersed in distilled water and, in a dark place, vernalized at 4° C. for 3 days. A solution of the sample in methanol was put in a 1.5 mL-microtube, and methanol was removed therefrom under reduced pressure. An aqueous solution of 0.5% agar (containing ½ MS medium inorganic salts) at 70° C. was added thereto and stirred, and subsequently the obtained mixture was placed in a 96-well plate to prepare the medium containing the sample. All samples were prepared so as to have a concentration of 3 µM of the compound in Examples 1 to 9 and Comparative Example 1. Further, when ABA is applied, the ABA concentration was adjusted to 0.3 µM. 20 to 30 vernalized seeds of thale cress were planted in each well and cultured at 22° C. under continuous light to monitor the number of seeds germinated over time. The germination rate was calculated by the following formula (1). Note that those cultured in medium prepared using methanol in the same manner were used as controls. The results are shown in Table 1. It was revealed that the seed germination rates decreased by ABA are recovered when the compounds of Examples 1 to 9 were co-applied with ABA.

Germination rate (%)=Number of seeds germinated/ Number of seeds planted×100     (1)

TABLE 1

| Sample | Germination rate (%) | | | |
|---|---|---|---|---|
| | 24 Hours later | 36 Hours later | 48 Hours later | 60 Hours later |
| Control | 0 | 86 | 100 | 100 |
| Example 1 | 0 | 86 | 100 | 100 |
| Example 2 | 11 | 27 | 77 | 100 |
| Example 3 | 0 | 13.3 | 60 | 71.1 |
| Example 4 | 8 | 33 | 75 | 92 |
| Example 5 | 5 | 37 | 79 | 95 |
| Example 6 | 0 | 17 | 75 | 92 |
| Example 7 | 0 | 86 | 100 | 100 |
| Example 8 | 0 | 60 | 100 | 100 |
| Example 9 | 1 | 88 | 100 | 100 |
| Comparative Example 1 | 0 | 85 | 100 | 100 |
| 03 µM ABA | 0 | 0 | 16.2 | 32.6 |
| 0.3 µM ABA + Example 1 | 0 | 79 | 100 | 100 |
| 0.3 µM ABA + Example 2 | 9 | 22 | 53 | 89 |
| 0.3 µM ABA + Example 3 | 0 | 6.9 | 20.7 | 48.3 |
| 0.3 µM ABA + Example 4 | 0 | 29 | 58 | 100 |
| 0.3 µM ABA + Example 5 | 0 | 30 | 67 | 100 |
| 0.3 µM ABA + Example 6 | 7 | 28 | 52 | 72 |
| 0.3 µM ABA + Example 7 | 0 | 76 | 100 | 100 |
| 0.3 µM ABA + Example 8 | 0 | 0 | 23 | 89 |
| 0.3 µM ABA + Example 9 | 0 | 60 | 100 | 100 |

TABLE 1-continued

| Sample | Germination rate (%) | | | |
|---|---|---|---|---|
| | 24 Hours later | 36 Hours later | 48 Hours later | 60 Hours later |
| 0.3 µM ABA + Comparative Example 1 | 0 | 28 | 67 | 89 |

The concentrations are all 3 µM in Examples and Comparative Example.

[Test Example 2] Thale Cress Seed Germination Test (2)

The same test was carried out as in Test Example 1 with the concentrations of the compound of Example 1 for treatment varying from 0.3 µM to 30 µM. The results are shown in FIG. 1. It was revealed that the seed germination rates decreased by ABA are recovered also in these concentrations range when the compound of Example 1 was co-applied with ABA.

Similarly, the same test was carried out with the concentrations of the compound of Example 2 for treatment varying from 0.3 µM to 30 µM. It was revealed that the seed germination rates decreased by ABA are recovered also in these concentrations range when the compound of Example 2 was co-applied with ABA.

[Test Example 3] Lettuce and Bok Choy Seed Germination Test

The same test was carried out as in Test Example 2 using lettuce (*Lactuca saliva*) and bok choy (*Brassica rapa* var. *chinensis*) in place of thale cress. The compounds of Examples 1 and 2 co-applied with ABA also recovered the seed germination rates once decreased by ABA for the seeds of lettuce and bok choy.

[Test Example 4] Comparison of the Compound of Example 1 and the Compound of Comparative Example 1

Figure 2:
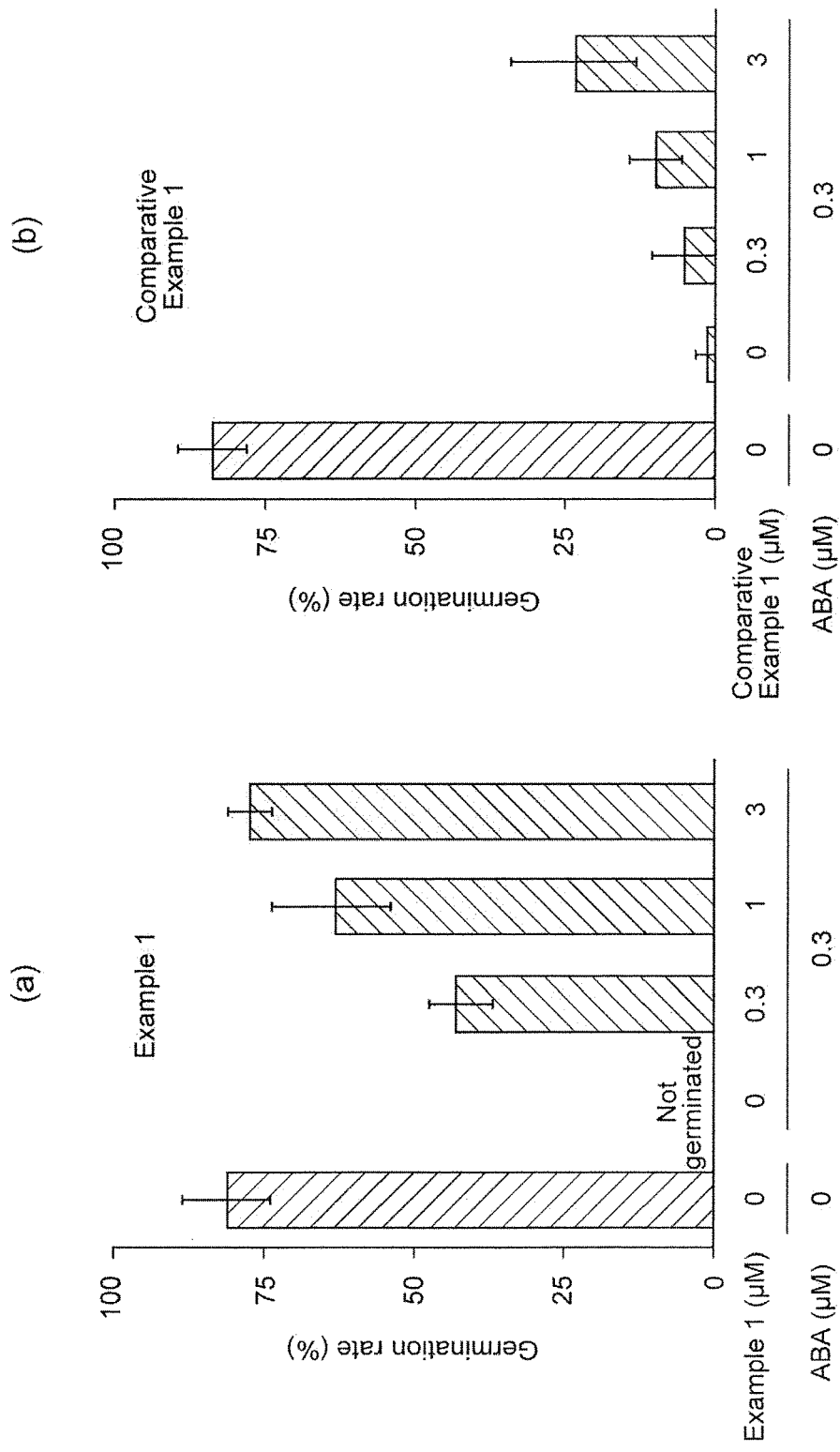
FIG. 2 includes graphs showing the results of the influence of the compounds of Example 1 and Comparative Example 1 on the seed germination of thale cress, for comparison.

The same test was carried out as in Test Example 2 with the concentrations of the compounds for treatment varying from 0.3 µM to 3 µM to compare the recovery effects on seed germination rate of the compound of Example 1 and the compound of Comparative Example 1. The results are shown in FIG. 2. It was revealed that the compound of Example 1 excels in the recovery effect on seed germination rate more than the compound of Comparative Example 1.

[Test Example 5] Protein Dephosphorylation Enzyme Activity Test

Figure 3:
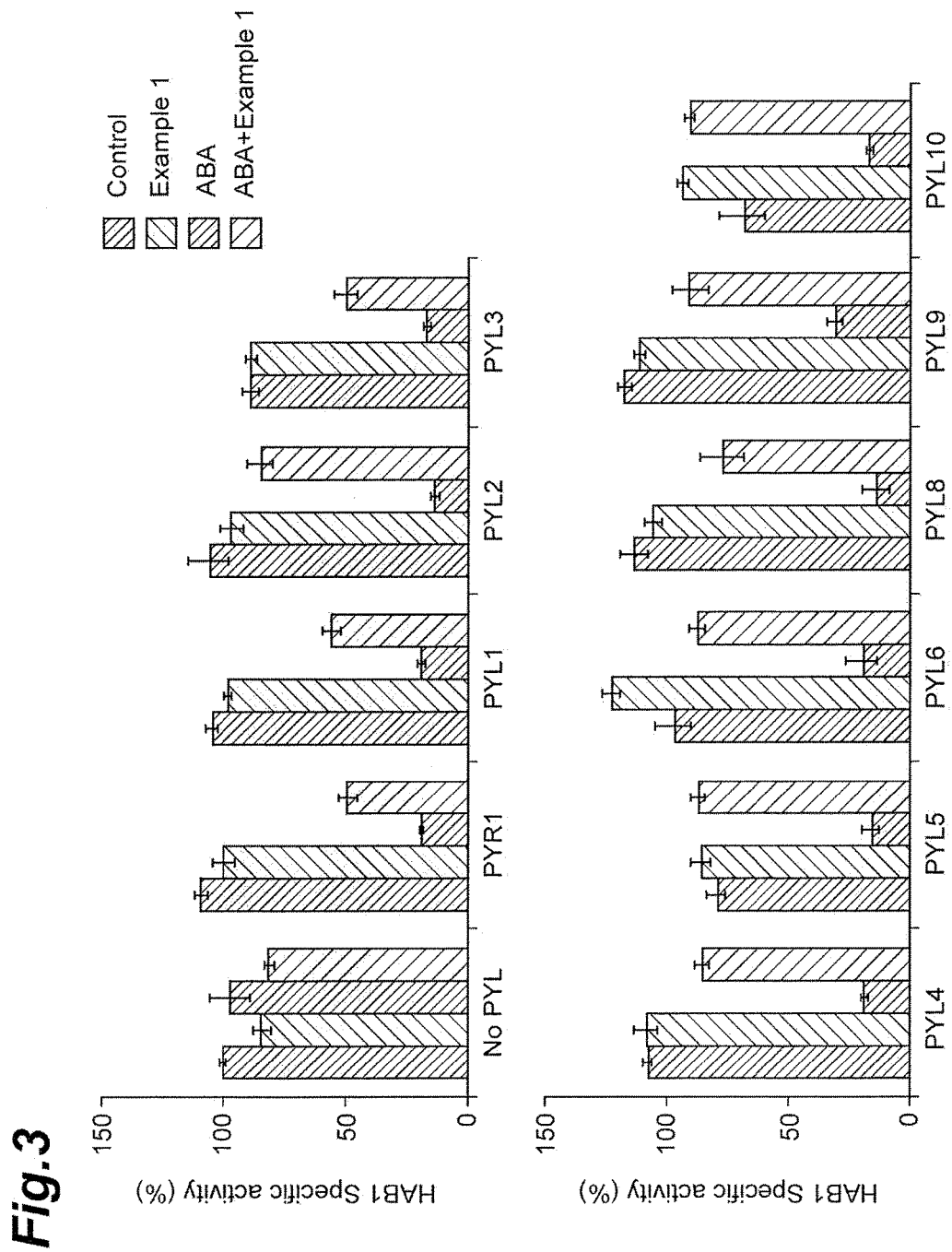
FIG. 3 includes graphs showing the examination results of the influence of the compound of Example 1 on the abscisic acid receptor.

A plasmid (pGex-2T-GST-HAB1 or pET28-6×His-PYL) encoded with PYR/PYL/RCAR proteins (PYL, abscisic acid receptor) or protein dephosphorylation enzyme HAB1 of thale cress was transformed to *Escherichia coli* (HAB1: BL21(DE3)pLysS, PYL:BL21-codonplus(DE3)-RIPL). Isopropyl-β-thiogalactopyranoside was added to the culture broth, which had been subjected to pre-culture (30° C., 180 rpm, 15 hours) and main culture (30° C., 180 rpm, 4 hours), and the protein-expressed (16° C., 150 rpm, 18 hours) crude enzyme solution was purified using FPLC thereby preparing the recombined PYL (PYR1, PYL1-6, PYL8-10) and HAB1. β-Mercaptoethanol, a manganese chloride aqueous solution, HAB1, PYL, a solution of the sample in dimethylsulfoxide and ultrapure water were sequentially added to a 96-well plate, allowed to stand at 22° C. for 30 minutes. Subsequently p-nitrophenylphosphate, which is the artificial substrate of HAB1, was added thereto to start the reaction, and the plate was placed in a microplate reader (TECAN, Infinite™ N200 NanoQuant). The absorbance at 405 nm due to p-nitrophenol, which is the hydrolysate of p-nitrophenylphosphate, was measured 3 minutes later from the reaction initiation, and HAB1 activity was calculated by the following formula (2). Note that the fraction to which only dimethylsulfoxide was added was considered to be the control and the activity thereof was defined as 100%. The results are shown in FIG. 3 and Table 2. It was revealed that the compounds of Example 1 and 4 to 9 act as the antagonist against the ABA receptor.

HAB1 specific activity (%)=Absorbance when sample was added/Absorbance of control×100 (2)

TABLE 2

| | HAB1 Specific activity (%) | | | | | | | | | |
|---|---|---|---|---|---|---|---|---|---|---|
| Sample | None | PYR1 | PYL1 | PYL2 | PYL3 | PYL4 | PYL5 | PYL6 | PYL8 | PYL9 | PYL10 |
| Example 1 | 83.8 | 99.6 | 98.1 | 96.6 | 88.6 | 108 | 85.8 | 122 | 105 | 111 | 93.7 |
| ABA | 97 | 18.6 | 18.6 | 13.1 | 16.8 | 18.2 | 15.5 | 19.5 | 13.9 | 31 | 16.2 |
| ABA+ Example 1 | 81 | 49 | 55.6 | 84.8 | 49.2 | 853 | 87 | 87.6 | 76.9 | 90 | 90.7 |
| Example 4 | — | 55.4 | — | — | — | — | — | — | — | — | — |
| Example 5 | — | 92.3 | — | — | — | — | — | — | — | — | — |
| Example 6 | — | 87.9 | — | — | — | — | — | — | — | — | — |
| Example 7 | — | 95.7 | 136 | 133 | 121 | 119 | 85.5 | 93.5 | 98.5 | — | 99.0 |
| Example 8 | — | 105 | — | — | — | — | — | — | — | — | — |
| Example 9 | — | 87.8 | — | — | — | — | — | — | — | — | — |
| ABA+ Example 4 | — | 36.7 | — | — | — | — | — | — | — | — | — |
| ABA+ Example 5 | — | 50.5 | — | — | — | — | — | — | — | — | — |
| ABA+ Example 6 | — | 41.5 | — | — | — | — | — | — | — | — | — |
| ABA+ Example 7 | — | 62.6 | 87.7 | 113 | 61 | 101 | 74.6 | 61.0 | 98.7 | — | 82.5 |
| ABA+ Example 8 | — | 62.9 | — | — | — | — | — | — | — | — | — |
| ABA+ Example 9 | — | 32.1 | — | — | — | — | — | — | — | — | — |

— Not measured

[Test Example 6] Bonding Affinity Measurement Test Using an Isothermal Titration Calorimeter A sodium phosphate buffer solution of a recombined PYL5 was prepared in the same procedure as in Test Example 5, and put in a reaction cell of an isothermal titration calorimeter (GE Healthcare, MicroCal iTC200), and a sodium phosphate buffer solution of the compound of Example 1 was put in the syringe. Then, the calorimeter was set to 20° C. and the measurement was carded out. The same measurement as above was also carried out for the compounds of Examples 7 to 9. Table 3 shows the results, with the results when the sodium phosphate buffer solution of ABA or the compound of Comparative Example 1 as the reference for comparison was used. Dissociation constant Kds of the compounds of Examples 1 and 7 to 9 are lower than those of ABA and the compound of Comparative Example 1 thereby revealing that the affinity of these compounds to the ABA receptor is higher.

TABLE 3

| Sample | Kd (μM) | ΔH (kcal/mol) | −TΔS (kcal/mol) | ΔG (kcal/mol) |
|---|---|---|---|---|
| ABA | 0.88 ± 0.11 | −7.8 ± 0.1 | −0.3 | −8.1 ± 0.1 |
| Example 1 | 0.07 ± 0.02 | −7.9 ± 0.1 | −1.7 | −9.6 ± 0.1 |
| Comparative Example 1 | 0.48 ± 0.10 | −9.7 ± 0.2 | 1.2 | −9.6 ± 0.1 |
| Example 7 | 0.07 ± 0.02 | −5.5 ± 0.1 | −4.2 | −9.6 ± 0.2 |
| Example 8 | 0.18 ± 0.01 | −4.9 ± 0.1 | −4.1 | −9.0 ± 0.1 |
| Example 9 | 0.36 ± 0.07 | −6.7 ± 0.1 | −2.0 | −8.6 ± 0.1 |

[Test Example 7] Male Cress Growth Test

Seeds of thale cress (*Arabidopsis thaliana*, Col-0) were sequentially immersed for 1 minute respectively in 500 μL of an aqueous solution of 5% bleach+1% SDS, 500 μL of a 70% aqueous solution of ethanol and 500 μL of a 70% aqueous solution of ethanol, washed five times in 1 mL of sterilized water, and then suspended in a 0.1% aqueous solution of agar. 25 mL each of germination medium (containing ½ MS medium inorganic salts) sterilized in an autoclave was added to a sterilized plastic petri dish, in which 60 to 80 seeds suspended in the 0.1% aqueous solution of agar were planted and, in a dark place, the seeds were vernilized at 4° C. for 3 days. The seeds were cultured at 22° C. under continuous light for 10 days. 40 g Path of sterilized soil (organic culture soil:vermiculite=1:1) was added to a plastic pot (50 mm×50 mm×50 mm, 35 mm bottom surface×35 mm height). Six plastic pots thus provided were placed in a 3000 mL-tray, 300 mL (depth 10 mm) of an aqueous solution of 1000-fold diluted HYPONeX (tradename (registered trademark), product of HYPONeX JAPAN CORP., LTD.) was added thereto and five roots each of thale cress seedlings were transplanted from the plastic petri dish. The seedlings were cultured at 22° C. under conditions of 16 hour light period-8 hour dark period, and 1 mL of an aqueous solution (prepared so as the final concentration of the compound of Example 7 to be 50 μM) of 0.1% DMSO (containing the compound of Example 7)+0.1%

Approach BI (tradename (registered trademark), product of Kao Corporation) was sprayed once a day. Further, 300 mL of an aqueous solution of 2000-fold diluted HYPONeX was added every week. The same treatment as above was carried out using the compound of Comparative Example 1. Note that the seedlings, to which 1 mL of an aqueous solution of 0.1% DMSO+0.1% Approach BI without containing the above compound was sprayed once a day, were used as controls. Furthermore, a test was carried out under the same conditions as above in which ABA was added to 1 mL of an aqueous solution of 0.1% DMSO (containing the compound of Example 7, containing the compound of Comparative Example 1, or not containing these compounds)+0.1% Approach BI (prepared so as to have a final concentration of 50 μM when containing the compound) to a final concentration of 5 μM, the obtained solution being sprayed once a day. The growth conditions of thale cress were compared after three weeks' culture and found that, when only ABA was applied, the growth of thale cress was notably suppressed. Contrary, when the compound of Comparative Example 1 and ABA were co-applied, the growth suppression effect of ABA was not substantially improved. However, when the compound of Example 7 and ABA were co-applied, the growth suppression effect by ABA was notably improved and the thale cress growth was recovered to the same extent as the controls.

The invention claimed is:

1. A compound of formula (IV) or a salt thereof:

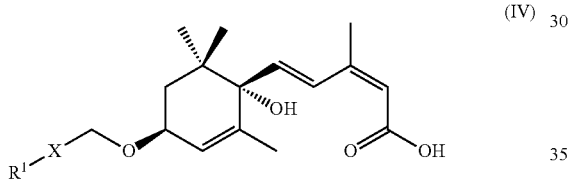

(IV)

wherein X is an ethenylene group or an ethynylene group, $R^1$ is a hydrogen atom, a phenyl group or a naphthyl group, and the phenyl group and naphthyl group each optionally have a substituent selected from the group consisting of a halogen atom, a hydroxyl group, a C1-6 alkyl group, a C1-6 alkyl group substituted with a halogen atom, a C1-6 alkoxy group, an acetyl group, an amino group, an acetylamino group, a phenyl group and a pentafluorosulfanyl group.

2. The compound or the salt thereof according to claim 1, being a compound of formula (I) or a salt thereof:

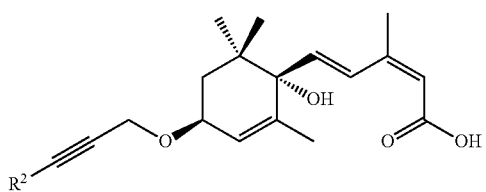

(I)

wherein $R^2$ is a hydrogen atom, a phenyl group or a naphthyl group, and the phenyl group and naphthyl group each optionally have a substituent selected from the group consisting of a halogen atom, a hydroxyl group, a C1-6 alkyl group, a C1-6 alkyl group substituted with a halogen atom, a C1-6 alkoxy group, an acetyl group, an amino group, an acetylamino group and a phenyl group.

3. An inhibitor of an abscisic acid receptor, comprising the compound or the salt thereof according to claim 1.

4. A plant growth regulator comprising the compound or the salt thereof according to claim 1.

5. An inhibitor of an abscisic acid receptor, comprising the compound or the salt thereof according to claim 2.

6. A plant growth regulator comprising the compound or the salt thereof according to claim 2.

7. A compound of formula (IV) or a salt thereof:

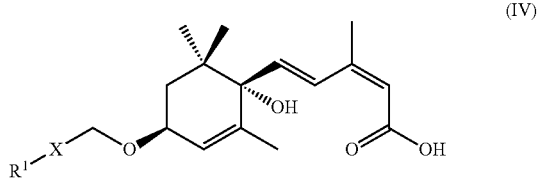

(IV)

wherein X is an ethylene group, $R^1$ is a phenyl group or a naphthyl group, and the phenyl group and naphthyl group each optionally have a substituent selected from the group consisting of a halogen atom, a hydroxyl group, a C1-6 alkyl group, a C1-6 alkyl group substituted with a halogen atom, a C1-6 alkoxy group, an acetyl group, an amino group, an acetylamino group, a phenyl group and a pentafluorosulfanyl group.

8. An inhibitor of an abscisic acid receptor, comprising the compound or the salt thereof according to claim 7.

9. A plant growth regulator comprising the compound or the salt thereof according to claim 7.

10. The compound or the salt thereof according to claim 2, wherein $R^2$ is a p-tolyl group.

11. An inhibitor of an abscisic acid receptor, comprising the compound or the salt thereof according to claim 10.

12. A plant growth regulator comprising the compound or the salt thereof according to claim 10.

* * * * *